United States Patent [19]

Soernmo et al.

[11] Patent Number: 5,564,428
[45] Date of Patent: Oct. 15, 1996

[54] METHOD AND APPARATUS FOR ENHANCING THE SIGNAL-TO-NOISE RATIO OF ECG SIGNALS

[75] Inventors: Leif Soernmo, Lund; Thomas Ohlsson, Haesselby; Roozbeh Atarius, Lund, all of Sweden

[73] Assignee: Siemens-Elema AB, Solna, Sweden

[21] Appl. No.: 271,714

[22] Filed: Jul. 7, 1994

[30] Foreign Application Priority Data

Jul. 16, 1993 [SE] Sweden .................................. 9302436

[51] Int. Cl.$^6$ .................................................. A61B 5/0428
[52] U.S. Cl. .................................................................. 128/696
[58] Field of Search .................................. 128/696, 712; 364/413.06

[56] References Cited

U.S. PATENT DOCUMENTS

| | | | |
|---|---|---|---|
| 4,732,158 | 3/1988 | Sadgh .............................. | 364/413.06 |
| 4,769,760 | 9/1988 | Krell et al. ...................... | 364/413.06 |
| 4,802,491 | 2/1989 | Cohen et al. . | |
| 5,092,341 | 3/1992 | Kelga ............................... | 364/413.06 |
| 5,226,424 | 7/1993 | Bible . | |
| 5,255,186 | 10/1993 | Steinhaus et al. ................ | 364/413.06 |

FOREIGN PATENT DOCUMENTS 0424607  5/1991  European Pat. Off. .

OTHER PUBLICATIONS

"Alignment Methods for Averaging of High-Resolution Cardiac Signals: A Comparative Study of Performance," Jané et al., IEEE Trans. on Biomed. Eng., vol. M38, No. 6, Jun. 1991, pp. 571–579.

"The Performance of Information–Theoretic Criteria in Detecting the Number of Independent Signals in Multilead ECGs", Uigen et al., Meth. Inform. Med., vol. 31, 1992, pp. 256–262.

"Theory and Practice of A Posteriori Wiener Filtering of Average Evoked Potentials", de Weerd et al., Biol. Cybern., 30 (1978), pp. 81–94.

"A Posteriori Time–Varying Filtering of Averaged Evoked Potentials", de Weered et al., Biol. Cybern., 41 (1981) pp. 233–234.

Primary Examiner—William E. Kamm
Attorney, Agent, or Firm—Hill, Steadman & Simpson, A Professional Corporation

[57] ABSTRACT

In a method for enhancing the signal-to-noise ratio of ECG signals, A/D-converted signals from a number of cardiac cycles are time-synchronized to form a signal ensemble, and the correlation between the signals in the ensemble is determined in time intervals, comprising at least two samples, during at least a part of the cardiac cycles. A device for enhancing the signal-to-noise ratio of ECG signals, includes circuitry for recording, A/D-converting and other processing of the ECG signals. A synchronization unit is arranged to time-synchronize the signals from a plurality of cardiac cycles to form a signal ensemble, and a calculator unit controlled by a window unit determines the correlation between the signals in the ensemble in time intervals, comprising at least two samples, during at least a part of the cardiac cycles.

13 Claims, 2 Drawing Sheets

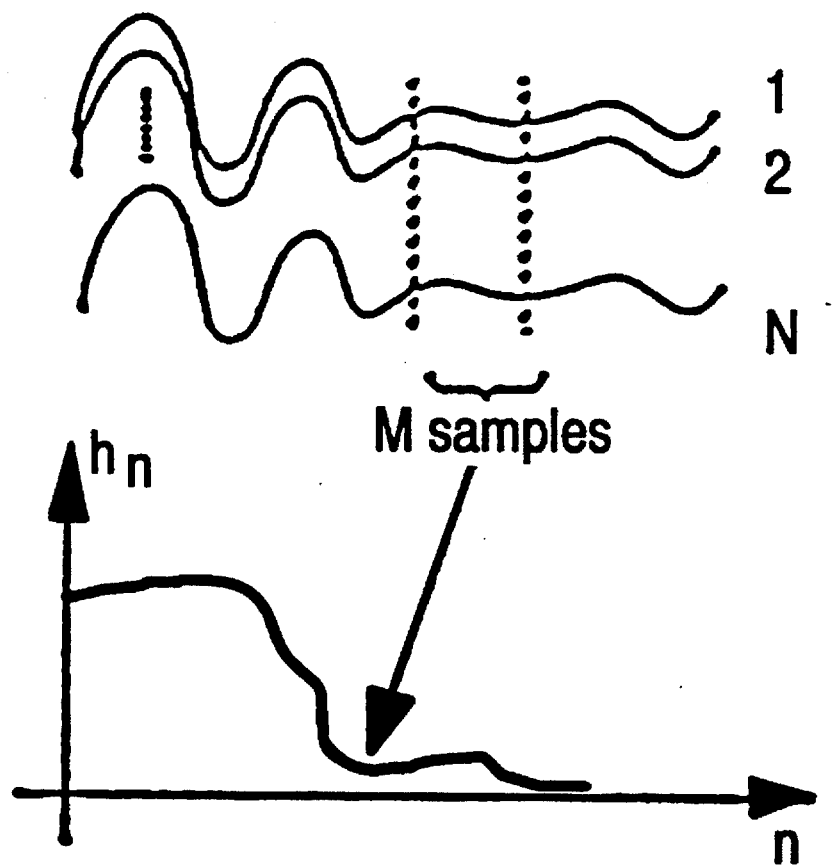

METHOD AND APPARATUS FOR ENHANCING THE SIGNAL-TO-NOISE RATIO OF ECG SIGNALS

BACKGROUND OF THE INVENTION

1. Field of the Invention

The present invention relates to a method and a device for enhancing the signal-to-noise ratio of ECG signals.

2. Description of the Prior Art

ECG signals recorded on the exterior of the body always contain extensive noise originating from muscular activity, digitization of the recorded analog ECG signal, the recording instruments and influence from the power supply. Using modern technology, however, the two latter sources of noise can be largely eliminated. Noise from the muscular activity of the patient and the digitization procedure, however, often drowns out low-amplitude signal components in the ECG signal.

In an effort to reduce noise, and thus to improve the signal-to-noise ratio for these low-amplitude signal components, it is known to subject the ECG signals to different kinds of averaging procedures. Time-varying Wiener filtration has also been attempted in order to enhance the signal-to-noise ratio, see Weerd and Martens: "Theory and Practice of A Posteriori Wiener Filtering of Average Evoked Potentials", Biol. Cybern., 30, pp. 81–94, (1978), and Weerd and Kap.: "A Posteriori TimeVarying Filtering of Averaged Evoked Potentials", Biol. Cybern., 41, pp. 223–234, (1981). This technique is based on the estimated signal and noise effects determined for different frequencies. In this process, some spectral loss is unavoidable in the Fourier transform procedure utilized. With low signal-to-noise ratios, this method also results in a consistently erroneous identification of the sought signal contained in the noise.

SUMMARY OF THE INVENTION

An object of the present invention is to provide a method and apparatus which achieve additional enhancement of the signal-to-noise ratio which, in turn, permits identification of low-amplitude signal components in the ECG signal, such as so-called "late potentials", without use of Fourier transform with all its disadvantages.

The above object is achieved in accordance with the principles of the present invention in a method and apparatus wherein incoming ECG signals from a plurality of cardiac cycles are analog-to-digital converted and the digital signals from the respective cardiac cycles are time-synchronized to form a signal ensemble, and wherein a correlation between the signals comprising the ensemble is determined in time intervals, the time intervals including at least two samples, during at least a part of the cardiac cycles.

The correlation can then be used to determine a filter characteristic for use in a filter for filtering the ECG signals, which is, at any given time, an optimum characteristic.

In the present invention representative parts of ECG signals from a plurality of cardiac cycles are thus filtered in a filter, the characteristics of which are related to the prevailing signal-to-noise ratio.

Thus according to the invention, the signals from a plurality of cardiac cycles are time-synchronized to form a signal ensemble, and the correlation across the signal ensemble is determined, although not the time correlation. In this way the size of the resulting cross-correlation matrix is reduced such that determination of the optimum filter characteristic at every point of time is made possible.

According to an advantageous embodiment of the apparatus of the invention, the correlation between the signals in the signal ensemble is determined in successive, overlapping intervals with the aid of a window unit. The optimum filter characteristic at any given moment is thus determined though short-period analysis. In this way time distortion (smearing) is avoided.

DESCRIPTION OF THE DRAWINGS

FIG. 3 shows curves illustrating the technique utilized by the invention.

DESCRIPTION OF THE PREFERRED EMBODIMENTS

Figure 1:
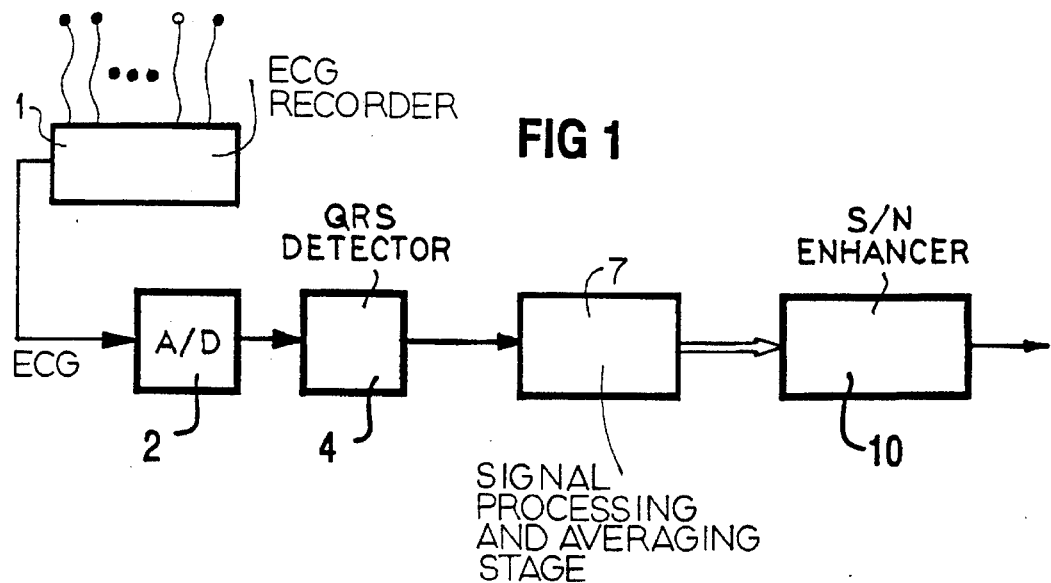
FIG. 1 is an overview block diagram of the device according to the invention.

As shown in FIG. 1, ECG signals obtained from an ECG recorder 1 are converted into digital form in an A/D converter 2, and QRS complexes in the digital signal are detected in a detector 4 and the detected complexes are supplied to a signal processing and averaging stage 7. Averaged digital signal values are formed in an averager 6 (FIG. 2), and an interval or time window is determined in a window unit 8 (FIG. 2), the time window is used for enhancing the signal-to-noise ratio (S/N) of the ECG signal during at least a part of each cardiac cycle in an S/N enhancer 10.

Figure 2:
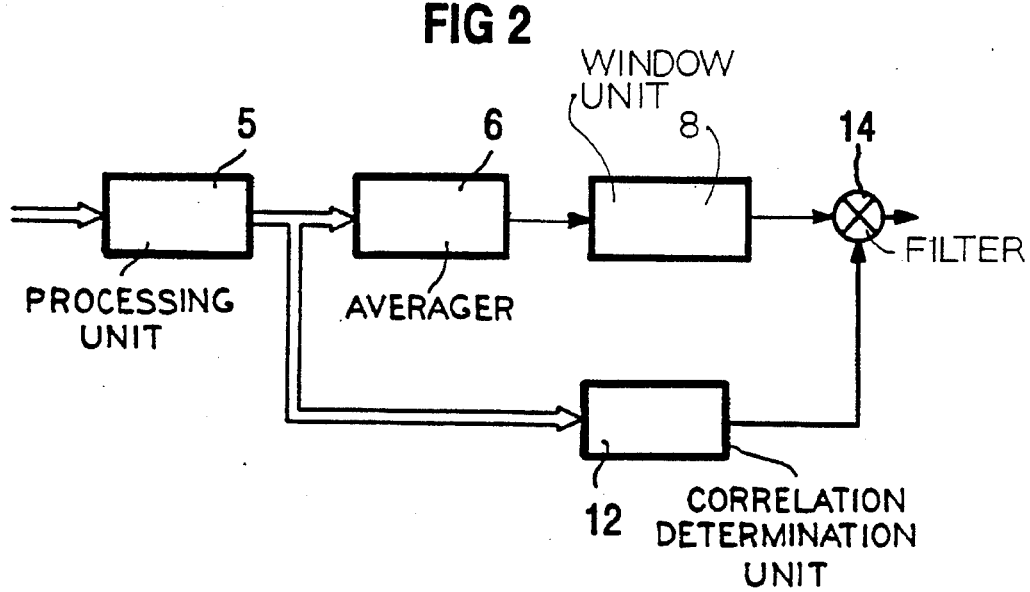
FIG. 2 is a block diagram showing the signal processing and averaging stage of the device in FIG. 1 in greater detail.

The units 6, 8 and 10 are described in greater detail with reference to FIG. 2.

Recorded ECG signals from a plurality of cardiac cycles are time-synchronized so they form an ensemble of signals. The elimination of low-frequency components, which is performed by a high-pass filter with a low cut-off frequency, is essential in the determination of the optimum filter at any given moment. This high-pass filtering, with other signal processing including the aforementioned time-synchronization, takes place in a signal processing unit 5.

In the averager 6, average values over the signal ensemble are formed. Averaging need not be performed as a "pure" averaging of all the signals in the ensemble, but can be carried out in different other ways in order to "improve" the average value and provide a representative signal cycle. So, e.g., strongly deviating signals, in the ensemble could be omitted in the averaging, and/or the averaging could be performed, e.g., in successive, overlapping intervals determined by the window unit 8. Averaging could also consist of median determination.

In the correlation determination unit 12 the correlation between the individual signals in a time window in the ensemble of signals, set by the time window unit 8, is determined according to a Maximum Likelihood method. The ensemble correlation $\mu ml$ thereby obtained is given by the following equation:

$$\mu ML = \frac{\sum_{k=1}^{M} \left[ \sum_{i=1}^{N} Z_i(k)^2 - \sum_{i=1}^{N} z_i^2(k) \right]}{(N-1) \sum_{k=1}^{M} \sum_{i=1}^{N} z_i^2(k)}$$

in which $z_i$ denotes the $i^{th}$ filtered ECG signal,

N is the number of cardiac cycles considered and

M is the number of samples in the interval or time window.

The ensemble correlation thus determined is utilized for determining the optimum characteristics of a filter 14 for filtering the mean signal value obtained from the averager 6 in order to get as large a signal-to-noise ratio as possible. The optimum filter characteristic is determined for each successive interval or time window, thus the resulting filter 14 becomes time-dependent. The filter consequently has a certain weighting for each observation interval or sample. The filtration in the filter 14 is thereby reduced to multiplication by a weight function $h_n$ obtained from the correlation determination unit 12. This is illustrated in FIG. 3 which shows N signals in the signal ensemble and the resulting weighting function $h_n$, which determines the characteristic of the filter 14.

The momentarily optimum characteristic for the filter 14 achieved in this way is a non-frequency-selective filter, and the magnitude of the signal-to-noise ratio is used for determining the filter weightings. Since the signal-to-noise ratio is a function of the number of available cardiac cycles, the momentarily optimum filter characteristic, and accordingly the output signal, become a function of this parameter. This filter characteristic can also easily vary considerably if the number of cardiac cycles is low, however, this variation decreases as the number of utilized cardiac cycles increases.

With an increasing number of cardiac cycles N, the noise in the averaged signal decreases, a circumstance which contributes to enhancement of the signal-to-noise ratio at the same time as the momentarily optimum filter characteristic is improved through the access to more information, as mentioned above. Both these effects consequently contribute to a reduction of fluctuations in the output signal from the filter as the number of cardiac cycles increases.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for enhancing the signal-to-noise ratio of ECG signals comprising the steps of:

obtaining analog ECG signals from a plurality of cardiac cycles;

converting the analog ECG signals into digital ECG signals;

time-synchronizing the digital ECG signals from the respective cardiac cycles to form a signal ensemble;

determining a correlation between the ECG signals in said ensemble in time intervals comprising at least two samples during at least a part of said cardiac cycles; and employing said correlation to enhance the signal-to-noise ratio of the ECG signals.

2. A method as claimed in claim 1 wherein the step of determining the correlation between the signals comprises determining a set of weightings expressing said correlation between the signals, and wherein the step of enhancing said signal-to-noise ratio comprises filtering said ECG signals with a filter characteristic determined by said weightings.

3. A method as claimed in claim 1 further comprising forming an average value of said signals in said signal ensemble.

4. A method as claimed in claim 1 wherein the step of determining the correlation between the signals in said ensemble comprises determining the correlation between the signals in said ensemble in successive, overlapping time intervals.

5. A method as claimed in claim 4 wherein the step of determining the correlation between the signals in said ensemble in successive, overlapping time intervals produces weightings, and wherein the step of enhancing said signal-to-noise ratio comprises filtering said ECG signals with a filter characteristic determined by said weightings.

6. A method as claimed in claim 5 wherein the step of filtering the ECG signals comprises filtering the ECG signals with a time-variable filter characteristic determined by said weightings.

7. An apparatus for enhancing the signal-to-noise ratio of analog ECG signals, comprising:

means for recording analog ECG signals from a subject from a plurality of cardiac cycles;

means for converting the analog ECG signals into digital ECG signals;

means for time synchronizing the digital ECG signals from the respective cardiac cycles to form a signal ensemble;

means for setting a time window comprising at least two samples of said digital ECG signals;

means for correlating the digital ECG signals in said ensemble within said time window during at least a part of said cardiac cycles; and means for enhancing the signal-to-noise ratio of the ECG signals dependent on the correlation between the signals in the ensemble.

8. An apparatus as claimed in claim 7 wherein said means for correlating comprise means for producing a weighting function and wherein said means for enhancing comprises a filter having a filter characteristic determined by said weighting function.

9. An apparatus as claimed in claim 7 further comprising averaging means, controlled by said means for time-synchronizing, for forming an average value of said signals in said ensemble.

10. An apparatus as claimed in claim 7 further comprising averaging means, controlled by said means for setting a time window, for averaging said signals in said signal ensemble.

11. An apparatus as claimed in claim 7 wherein said means for setting a time window comprises means for controlling said means for correlating for determining the correlation of said ensemble in successive, overlapping time intervals.

12. An apparatus as claimed in claim 7 wherein said means for correlating comprises a maximum likelihood estimator.

13. An apparatus for enhancing the signal-to-noise ratio of analog ECG signals comprising:

means for recording analog ECG signals over a plurality of cardiac cycles of a subject;

means for converting the analog ECG signals into digital ECG signals;

means for time-synchronizing the digital ECG signals from the respective cardiac cycles in said plurality of cardiac cycles to form a signal ensemble;

means for setting a time window comprising at least two samples of said digital ECG signals;

means for determining the correlation between the digital ECG signals in said ensemble in said time interval; and means for filtering said ECG signals, for enhancing the signal-to-noise ratio, with a filter characteristic dependent on the correlation between said signals in said ensemble.

* * * * *